(12) United States Patent
Yamada

(10) Patent No.: US 7,837,707 B2
(45) Date of Patent: Nov. 23, 2010

(54) INTERNAL PROCEDURE FOR CLOSING SINUS MEMBRANE PERFORATIONS

(76) Inventor: Jason M. Yamada, 29 Quarter Horse La., Rolling Hills Estates, CA (US) 90274

(*) Notice: Subject to any disclaimer, the term of this patent is extended or adjusted under 35 U.S.C. 154(b) by 742 days.

(21) Appl. No.: 11/895,813

(22) Filed: Aug. 28, 2007

(65) Prior Publication Data

US 2008/0161834 A1    Jul. 3, 2008

Related U.S. Application Data

(60) Provisional application No. 60/882,940, filed on Dec. 31, 2006.

(51) Int. Cl.
*A61B 17/08* (2006.01)
(52) U.S. Cl. .......... 606/213; 433/173; 433/215
(58) Field of Classification Search ......... 606/213, 606/151, 198–199; 433/173, 215; 623/23.72, 623/10
See application file for complete search history.

(56) References Cited

U.S. PATENT DOCUMENTS

| | | | | |
|---|---|---|---|---|
| 4,682,951 A * | 7/1987 | Linkow | | 433/173 |
| 5,306,304 A * | 4/1994 | Gendler | | 623/23.63 |
| 5,397,235 A * | 3/1995 | Elia | | 433/173 |
| 5,464,439 A * | 11/1995 | Gendler | | 128/898 |
| 5,547,378 A * | 8/1996 | Linkow | | 433/173 |
| 5,556,430 A * | 9/1996 | Gendler | | 128/898 |
| 5,685,716 A * | 11/1997 | Linkow | | 433/173 |
| 5,711,315 A * | 1/1998 | Jerusalmy | | 128/898 |
| 6,343,931 B1 * | 2/2002 | Regni, Jr. | | 433/175 |
| 6,799,970 B2 * | 10/2004 | Martin et al. | | 433/173 |
| 7,125,253 B2 * | 10/2006 | Kitamura et al. | | 433/173 |
| 7,662,188 B2 * | 2/2010 | Yamada | | 623/17.17 |
| 7,771,482 B1 * | 8/2010 | Karmon | | 623/17.17 |
| 2006/0084034 A1 * | 4/2006 | Hochman | | 433/173 |
| 2006/0287732 A1 * | 12/2006 | Pezeshkian | | 623/17.17 |
| 2008/0161835 A1 * | 7/2008 | Yamada | | 606/151 |
| 2008/0161934 A1 * | 7/2008 | Yamada | | 623/17.17 |
| 2008/0182225 A1 * | 7/2008 | Gordils Wallis | | 433/144 |
| 2008/0243123 A1 * | 10/2008 | Gordils Wallis et al. | | 606/80 |
| 2008/0319466 A1 * | 12/2008 | Eder | | 606/169 |
| 2009/0181343 A1 * | 7/2009 | Hernandez et al. | | 433/141 |
| 2010/0178631 A1 * | 7/2010 | Gordils Wallis et al. | | 433/82 |

* cited by examiner

*Primary Examiner*—Gary Jackson
*Assistant Examiner*—Son Dang
(74) *Attorney, Agent, or Firm*—Robert R. Meads

(57) ABSTRACT

An internal sinus procedure for patching a perforation in patient's sinus membrane comprising the steps of (i) creating an opening in the sinus floor of a patient to expose the portion of the sinus membrane including the perforation, (ii) inserting a quantity of a sinus membrane patching material through the opening to a location adjacent the sinus perforation and (iii) laterally expanding and forcing the patching material against the sinus membrane to seal the perforation.

2 Claims, 3 Drawing Sheets

INTERNAL PROCEDURE FOR CLOSING SINUS MEMBRANE PERFORATIONS

RELATED PATENT APPLICATIONS

The present application claims the benefit of U.S. Provisional Patent application Ser. No. 60/882,940 filed Dec. 31, 2006, which is herein incorporated by reference. The present application also relates to the subject matter of the concurrently filed U.S. patent application Ser. No. 11/895,823, entitled "Internal Sinus Manipulation (ISM) Procedure For Facilitating Sinus Floor Augmentation In Dental Procedures", which is incorporated herein by this reference.

BACKGROUND OF INVENTION

In the procedure described in the above-identified concurrently filed U.S. patent application, it is suggested that in forming an upward channel in the bone leading to the sinus floor of a patient, care should be taken to insure that the upward channel barely breaks through the existing bone without perforating the sinus membrane of the patient. The present invention is directed to a sinus membrane patching procedure that may be employed if a sinus membrane perforation should occur in the formation of the upward channel or is discovered as having been previously formed during an independent dental procedure or as a result of a physical accident suffered by the patient.

SUMMARY OF INVENTION

Basically, the procedure of the present invention comprises the steps of (i) creating an opening in the sinus floor of a patient to expose the portion of the sinus membrane including the perforation, (ii) inserting a quantity of a sinus membrane patching material through the opening to a location adjacent the sinus perforation and (iii) laterally expanding and forcing the patching material against the sinus membrane to seal the perforation.

The creation of the opening may be accomplished by the use of standard drills and drilling techniques and the like controlled to create an upward channel in the bone of the patient leading to the sinus floor. In this regard, the upper open end of the channel should extend to the base of the sinus floor and should be small enough to only expose the portion of the sinus membrane having the perforation.

If the perforation of the sinus membrane occurs during the formation of the upward channel and if it is desired to lift and laterally extend the sinus membrane prior patching of the sinus membrane, such lifting and lateral separation of the portion of sinus membrane from the sinus floor may be accomplished using a sinus lifting tool that includes a disk-shaped tip and an angled neck. The disk-shaped tip is designed to release the sinus membrane from the bony wall of sinus floor. The angled neck is designed to aid in the proper positioning of the working tip. An inflection portion of the angled neck extending from the working tip allows the clinician to feel the tension of the sinus membrane and to determine the amount of initial lateral and vertical membrane reflection. The procedure for membrane release and elevation should be continued until a planned amount of sinus extension is achieved and a pocket of desired size is defined.

The introduction of the sinus membrane patching material and the lateral expansion and forcing of the laterally extended material against the lower surface of the sinus membrane including the perforation may be accomplished using a patching material carrying instrument or insertion tool including a central support and laterally moveable outer supports spaced laterally outward of the central support. A preferred form of such an instrument is described and illustrated in detail in the concurrently filed U.S. patent application Ser. No. 11/895,814 entitled "Improved Sinus Membrane Patch Insertion Tool", incorporated herein by this reference.

BRIEF DESCRIPTION OF ACCOMPANYING DRAWINGS

Figure 1:
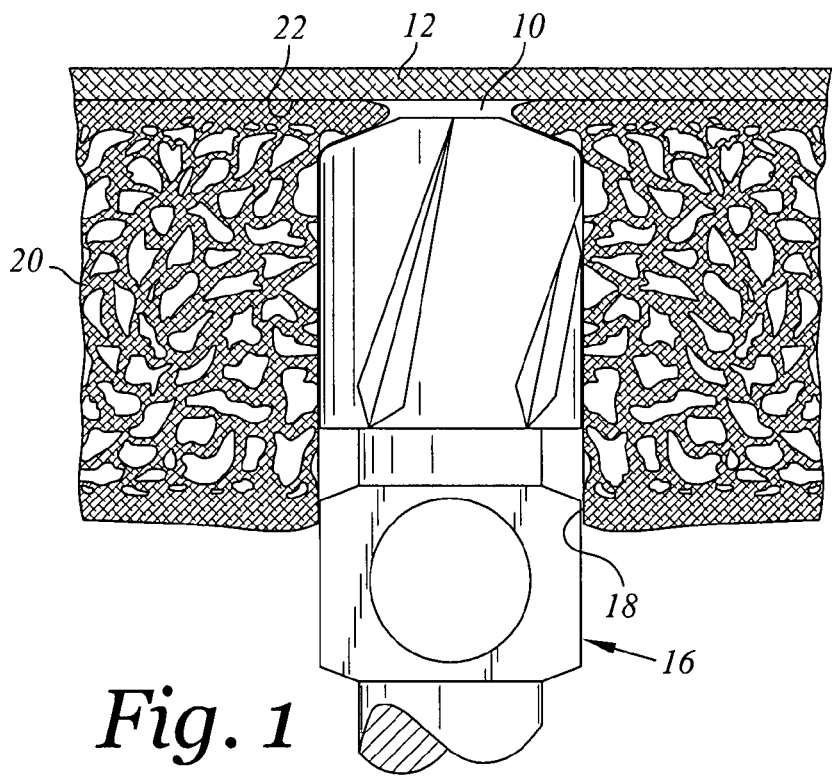
FIG. 1 is a fragmentary sectional side view illustrating the step of creating an opening in the sinus floor to expose the portion of a sinus membrane including the perforation as by employing a standard drill to form an upward channel through bone leading to the sinus floor.
Figure 3:
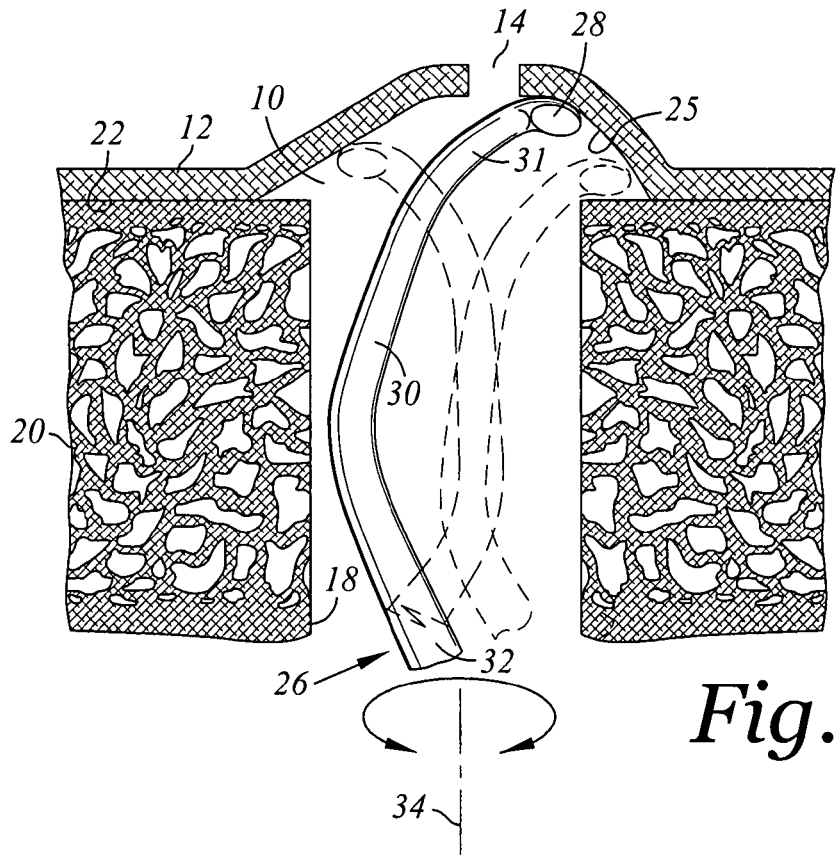

FIG. 3 is a fragmentary sectional side view of the bone channel of FIG. 1 receiving a sinus-lifting tool that includes a disk-shaped tip and an angled neck simultaneously lifting and laterally separating the exposed portion of the sinus membrane from the sinus floor to form a relatively small pocket between the sinus membrane and the sinus floor with lateral movement and a turning of the sinus lifting tool about a vertically extending axis of rotation.

Figure 2:
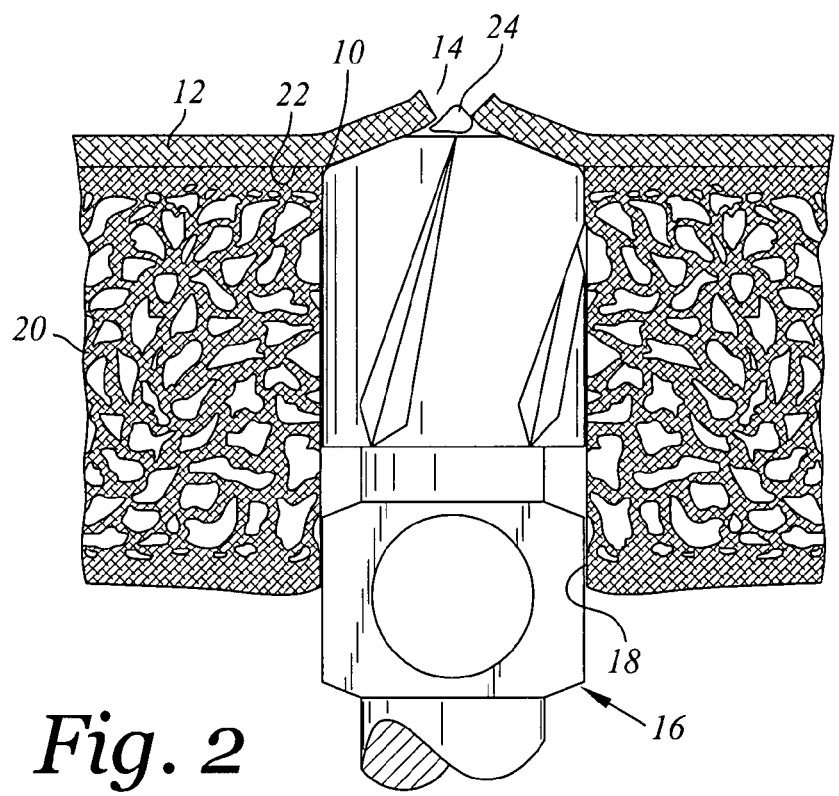
FIG. 2 is a fragmentary sectional side view showing the bone channel of FIG. 1 and illustrating the creation of a perforation in the sinus membrane by a fragment of bone during the drilling of the upward channel.
Figure 4A:
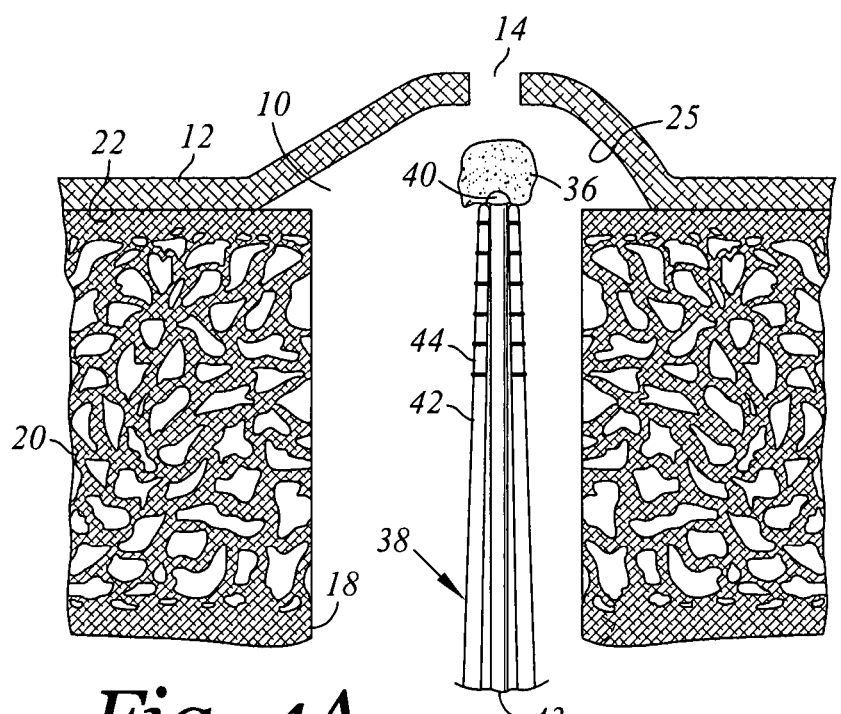

FIG. 4A is a fragmentary sectional side view of the bone channel of FIG. 3 receiving a sinus membrane patch insertion tool including a central support and laterally outward and moveable outer supports, the outer laterally moveable supports being laterally compressed against the central support to carry a quantity of sinus patching material upward in the bone channel to a location adjacent the lower surface of the lifted sinus membrane including the perforation formed in FIG. 2.

Figure 4B:
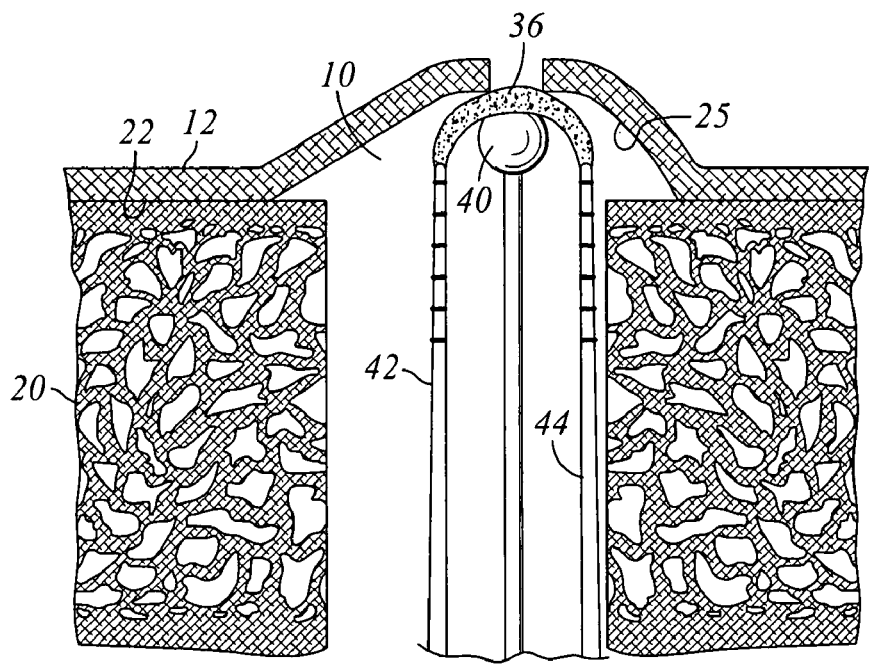

FIG. 4B is a fragmentary sectional side view of the bone channel and sinus patch insertion tool of FIG. 4A with the patching material engaging the sinus membrane over the perforation and the outer supports laterally separated from the central support, the patching material being extended laterally to form a patch sealing the perforation.

Figure 5:
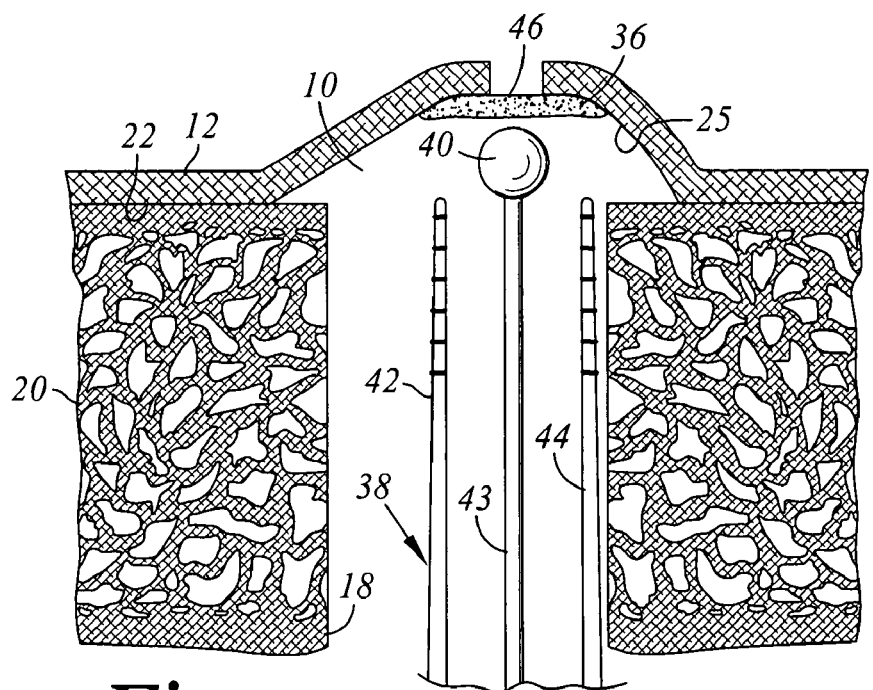

FIG. 5 is a fragmentary sectional side view of the bone channel and sinus patch insertion tool of FIG. 4B, the tool being lowered away from the sinus membrane leaving the patch in place.

DETAILED DESCRIPTION OF INVENTION

As previously indicated, in order to seal a sinus perforation according to the method of the present invention, an opening 10 is created in the sinus floor of a patient exposing the portion of the sinus membrane 12 including the perforation 14. This may be accomplished following a standard osteotomy drilling sequence using a surgical guide, a round marker and subsequent twist drills. Such a drilling procedure is depicted in FIG. 1 where a standard twist drill 16 is shown forming a channel 18 in bone 20 in the maxillary posterior area of a patient. Conventional twist drills or surgical round diamond burs can be used to drill up to the sinus floor 22, barely breaking through the existing bone and forming the desired opening 10 for exposing a preexisting sinus perforation or a perforation formed during a dental procedure such as shown in FIG. 2 where the drilling results in the sinus perforation 14 by the forcing of a bone fragment 24 into and through the sinus membrane 12. In either event, the sinus perforation 14 may be patched following the procedure of the present invention.

As illustrated in FIG. 3, the actual patching of the sinus perforation 14 may be preceded by a lifting and separation of the perforated sinus membrane 12 from the sinus floor 22 to form a pocket 25 between a lower surface of the sinus membrane 12 and the sinus floor. Preferably, such lifting and lateral separation is accomplished by the use of a sinus lifting tool 26 that includes a disk-shaped tip 28 and an angled neck 30 extending longitudinally from a handle portion 32. The disk-shaped tip 28 is designed to release the sinus membrane 12 from the bony wall of sinus floor 22. The angled neck 30 is designed to aid in the proper positioning of the working tip 28. An inflection portion 31 of the angle of the neck 30 extending from the working tip 28 allows the clinician to feel the tension of the sinus membrane 12 and to determine the amount of initial lateral and vertical membrane reflection. As illustrated in FIG. 3 by the solid, dashed and broken outlines of the tool 26, in the formation of the pocket 25 the tool 26 is simultaneously raised and turned back and forth on vertically extending axis 34 with the tip 28 simultaneously lifting and laterally separating the membrane 20 from the sinus floor 22 to form and enlarge the pocket 25. A preferred form of the tool 26 is described and illustrated more fully in the concurrently filed U.S. patent application Ser. No. 11/895,811, entitled "Improved Sinus Membrane Lifting and Lateral Separation Instrument", incorporated herein by this reference.

The patching of the perforation 14 in the sinus membrane 12 is then accomplished as shown in FIGS. 4A and B and FIG. 5. As there depicted, an appropriate standard sinus membrane patching material 36 is introduced through the opening 10 into the pocket 25 using a patching material insertion tool 38 designed to carry the material upward in the channel 18 and into the pocket to a location adjacent and just below the portion of the sinus membrane 12 including the perforation 14.

Basically, the insertion tool 38 comprises a central support 40 and outer supports 42 and 44 laterally spaced from and laterally moveable relative to the central support 40. The central support may comprise and is illustrated as comprising a ball 41 extending from a vertical support rod 43. A preferred form of the insertion tool 38 is described and illustrated more fully in the concurrently filed U.S. patent application Ser. No. 11/895,814, entitled "Improved Sinus Membrane Perforation Patching Material Carrying Instrument", incorporated herein by this reference.

As shown in FIG. 4A, during insertion of the sinus membrane patching material 36 through the opening 10 and into the pocket 25, the outer supports 42 and 44 are moved laterally against the central support 40 and the patching material is carried by the upper surface of the central support 40 and the upper surfaces of the outer supports. Thus supported, the patching material 36 is moved by the insertion tool 38 upward through the opening 10 and into the pocket 25 to a location adjacent to and immediately below the perforation 14 in the sinus membrane 12. As shown in FIG. 4B, the insertion tool 38 is then moved upwardly within the channel 18 until the patching material 36 is engages the sinus membrane 12 and extends slightly into the perforation 14. As this is accomplished, the outer supports 42 and 44 are released and moved laterally outward from the central support 40 to aid the central support 40 in laterally extending the patching material 36 to cover the lower surface of the sinus membrane adjacent the perforation and form a patch 46 as shown in FIG. 5.

In these regards, the standard patching material 36 is usually a semi-solid material as initially mounted on the insertion tool 38 as shown in FIG. 4A. When the patching material 36 engages the moist surface of the sinus membrane 12 it softens and becomes laterally extendable upon the release of the outer supports 42 and 44 and shapeable by the central support 40 to form a sticky adhesive patch 46 covering the perforation 14 and the adjacent lower surfaces of the sinus membrane 12 in response to movement of the central support 40.

While particular embodiments of the method and the preferred instruments employed in the method have been illustrated and described above, it is appreciated that changes and modifications may be made in the illustrated embodiments without departing from the spirit of the invention. Accordingly, the scope of present invention is to be limited only by the terms of the following claims.

The invention claimed is:

1. An internal procedure for closing a perforation in a patient's sinus membrane, comprising:
   creating an upward channel in bone leading to the sinus floor of the patient with an upper open end of the channel exposing a portion of the patient's sinus membrane sinus membrane including the perforation;
   selecting a patching material insertion instrument sized to extend upward into the channel and having an upwardly extending central support and upwardly extending outer supports slightly below and laterally spaced from the central support, the lateral supports being laterally movable toward and away from the central support;
   moving the outer supports inward against the central support and while the outer supports are so positioned applying a sinus membrane patching material to a top of the central support and upper surfaces of the outer supports and inserting the instrument upward within the channel until the patching material supported by the central and outer supports engage a lower surface of the sinus membrane and the perforation; and
   moving the outer supports away from the central support to laterally expand the patching material and form a patch covering the perforation.

2. The procedure of claim 1 wherein the sinus membrane is lifted and separated from the sinus floor following the creation of the upward channel and prior to the insertion of the instrument into the upward channel.

* * * * *